(12) United States Patent
Takatori et al.

(10) Patent No.: US 11,766,533 B2
(45) Date of Patent: Sep. 26, 2023

(54) BITE BLOCK AND GAS SENSOR KIT

(71) Applicant: Nihon Kohden Corporation, Tokyo (JP)

(72) Inventors: Fumihiko Takatori, Tokyo (JP); Masayuki Inoue, Tokyo (JP); Kenichiro Kabumoto, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 850 days.

(21) Appl. No.: 16/086,768

(22) PCT Filed: Jun. 2, 2017

(86) PCT No.: PCT/JP2017/020705
§ 371 (c)(1),
(2) Date: Sep. 20, 2018

(87) PCT Pub. No.: WO2017/217263
PCT Pub. Date: Dec. 21, 2017

(65) Prior Publication Data
US 2019/0105452 A1 Apr. 11, 2019

(30) Foreign Application Priority Data

Jun. 14, 2016 (JP) ................................. 2016-117770

(51) Int. Cl.
*A61M 16/04* (2006.01)
*A61B 1/00* (2006.01)
(Continued)

(52) U.S. Cl.
CPC ....... *A61M 16/049* (2014.02); *A61B 1/00154* (2013.01); *A61M 16/0488* (2013.01);
(Continued)

(58) Field of Classification Search
CPC ...................................... A61M 16/0488–0497
See application file for complete search history.

(56) References Cited

U.S. PATENT DOCUMENTS 3,508,543 A 4/1970 Aulicono
4,270,529 A 6/1981 Muto
(Continued)

FOREIGN PATENT DOCUMENTS

CN 101164633 A 4/2008
IL 172645 A 6/2010
(Continued)

OTHER PUBLICATIONS

Japanese Office action issued in Japanese Patent Application No. 2016-117770 dated Oct. 30, 2020.
(Continued)

*Primary Examiner* — Bradley H Philips
(74) *Attorney, Agent, or Firm* — Pearne & Gordon LLP (57) ABSTRACT

A bite block includes a hollow oral cavity insert part, a plate and a hollow outside part. The hollow oral cavity insert part is in contacts with an oral cavity of a subject at the time of attaching the bite block to the subject. The plate is formed in a flange shape extending from the oral cavity insert part. A hollow outside part includes an exposed portion which is exposed to an outside of the oral cavity at the time of attaching, and communicates with a hole of the oral cavity insert part. In the bite block, the hollow outside part includes at least one through hole with which an external device is attached to the bite block, on the exposed portion.

11 Claims, 12 Drawing Sheets

(51) Int. Cl.
*A61M 16/06* (2006.01)
*A61M 16/08* (2006.01)
(52) U.S. Cl.
CPC .... *A61M 16/0666* (2013.01); *A61M 16/0683* (2013.01); *A61M 16/085* (2014.02); *A61M 2202/0208* (2013.01)

(56) References Cited

U.S. PATENT DOCUMENTS

| | | | |
|---|---|---|---|
| 4,850,348 A * | 7/1989 | Pell | A61M 16/0488 128/207.15 |
| 2006/0278238 A1* | 12/2006 | Borody | A61M 16/08 128/859 |
| 2007/0006878 A1 | 1/2007 | Mackey et al. | |
| 2007/0068535 A1* | 3/2007 | Colman | A61B 1/00154 128/859 |
| 2008/0092901 A1 | 4/2008 | Kang | |
| 2010/0101567 A1* | 4/2010 | Hauge | A61M 16/0495 128/200.26 |
| 2010/0262033 A1* | 10/2010 | Colman | A61M 16/0493 600/532 |
| 2010/0317987 A1 | 12/2010 | Inoue et al. | |
| 2013/0061854 A1* | 3/2013 | Hauge | A61M 16/0493 128/207.14 |
| 2014/0034048 A1* | 2/2014 | Bruggeman | A61M 16/0465 128/200.26 |
| 2015/0283344 A1* | 10/2015 | Olympio | A61M 16/0493 128/200.26 |
| 2016/0256652 A1* | 9/2016 | Wiesman | A61M 16/0493 |
| 2017/0000641 A1* | 1/2017 | Arden | A61M 16/0493 |
| 2019/0125171 A1* | 5/2019 | Svard | A61M 16/0497 |

FOREIGN PATENT DOCUMENTS

| | | |
|---|---|---|
| IL | 205940 B | 4/2012 |
| JP | 5385599 B2 | 1/2014 |
| WO | 2005-016142 A1 | 2/2005 |
| WO | 2009-066277 A1 | 5/2009 |
| WO | 2015-042131 A2 | 3/2015 |
| WO | 2015-053313 A1 | 4/2015 |
| WO | WO-2015053313 A1 * | 4/2015 ......... A61M 16/049 |

OTHER PUBLICATIONS

International Search Report issued in Patent Application No. PCT/JP2017/020705 dated Aug. 17, 2017.
Written Opinion issued in Patent Application No. PCT/JP2017/020705 dated Aug. 17, 2017.
Chinese Office action issued in Chinese Patent Application No. 201780019793.3 dated Apr. 15, 2020.
European Office Action dated May 3, 2021 issued in Patent Application No. EP 17 731 316.0.
Japanese Office action issued in Japanese Patent Application No. 2016-117770 dated Apr. 3, 2020.

* cited by examiner

BITE BLOCK AND GAS SENSOR KIT

TECHNICAL FIELD

The present invention relates to a bite block which is connected with an external device including an overtube and the like, and a gas sensor kit.

BACKGROUND ART

A bite block, which a device for maintaining an open state of an oral cavity of a subject, is widely used when an inspection or the like is performed by using an endoscope. The bite block has a cylindrical shape, preferably, substantially conical shape, and the subject occludes the outer surface of the bite block.

PTL 1 discloses a bite block which accurately measures the respiratory state of the subject by avoiding an effect of secretion such as saliva. The bite block includes a cylindrical first wall having a hole into which a conduit is inserted, a second wall which surrounds the first wall and opposes an oral cavity, and a gas flow path to a sample port which is configured by a gap between the first wall and the second wall (FIGS. 1 and 2 in PTL 1). The bite block is configured such that the respiration information collection adapter is attachable therein and detachable therefrom, and a prong is attached in the respiration information collection adapter (FIG. 4 in PTL 1). Further, oxygen is supplied to the prong from an oxygen supplying source (paragraph [0024] in PTL 1).

CITATION LIST

Patent literature

[PTL 1]
Japanese Patent No. 5385599

SUMMARY OF INVENTION

Technical Problem

There is a case wherein the overtube is connected with the bite for a purpose of an inspection or a therapy. In the case where the overtube and the like are connected with the bite block, it is necessary to provide a connection structure with the overtube in the bite block. In a case where the connection structure is provided in the bite block, the structure of the opening surface, which is a surface which does not touch the subject, of the bite block may be complicated. For example, a shape in which the opening surface has a concavo-convex structure to be connected with the overtube is complicated. Accordingly, there is a risk that a soft tube and the like of the endoscope device are caught in the opening surface during the diagnosis with the endoscope, and the diagnosis cannot be performed smoothly.

In addition, there is a case in which an oxygen gas is administered with respect to the oral cavity of the subject while the treatment or the diagnosis is performed by using the bite block, so as to stabilize a respiratory state. In the configuration of PTL 1, a nasal adapter is connected with the bite block, and the oxygen gas is administered from a prong connected to the nasal adapter to a nostril. However, there is a case in which the oxygen gas is supplied not from the nostril (or in addition to the nostril) but from the oral cavity. In this case, when an attachment mechanism of the oxygen tube is provided in the bite block, the structure of the opening surface, a surface which does not touch the subject, of the bite block is complicated. For example, a shape in which the opening surface has a concavo-convex structure to be connected with the overtube is complicated.

There is a case where the structure of such a general bite block including the configuration of PTL 1 is not proper for connection with an external device such as an overtube or an oxygen tube.

Herein, a main object of the present invention is to provide a bite block having a structure which is proper for connection with an external device such as an overtube or an oxygen tube, and a gas sensor kit.

Solution to Problem

According to an aspect of the invention, a bite block includes a hollow oral cavity insert part, a plate and a hollow outside part. The hollow oral cavity insert part is in contacts with an oral cavity of a subject at the time of attaching the bite block to the subject. The plate is formed in a flange shape extending from the oral cavity insert part. The hollow outside part includes an exposed portion which is exposed to an outside of the oral cavity at the time of attaching, and communicates with a hole of the oral cavity insert part. In the bite block, the hollow outside part includes at least one through hole with which an external device is attached to the bite block, on the exposed portion.

The above-described bite block is configured such that the through hole is provided in the oral cavity outside arrangement part exposed outside at the time of mounting. The through hole acts as a connection mechanism which connects the bite block and the external device such as an overtube and an oxygen tube. When the through hole acts as a connection mechanism, the opening surface of the oral cavity outside arrangement part can be made in a simple shape. It is preferable that the opening surface has a planar shape. Accordingly, a case where a soft tube is caught in the opening surface is reduced even in a case where a treatment of an endoscope or the like is performed.

Advantageous Effects of Invention

The present invention can provide the bite block, which has a structure proper for connection with the external device such as the overtube or the oxygen tube, and the gas sensor kit.

DESCRIPTION OF EMBODIMENTS

First Embodiment

Hereinafter, a bite block 10 and a gas sensor kit 100 according to the embodiment of the present invention will be described with reference to the drawings. In the drawings, the same components are denoted by the same reference numerals and the same names, and the redundant explanation is not repeated. In addition, in order to facilitate understanding of the present invention, the size or the shape of each of components will be described after a proper adjustment.

Figure 1:
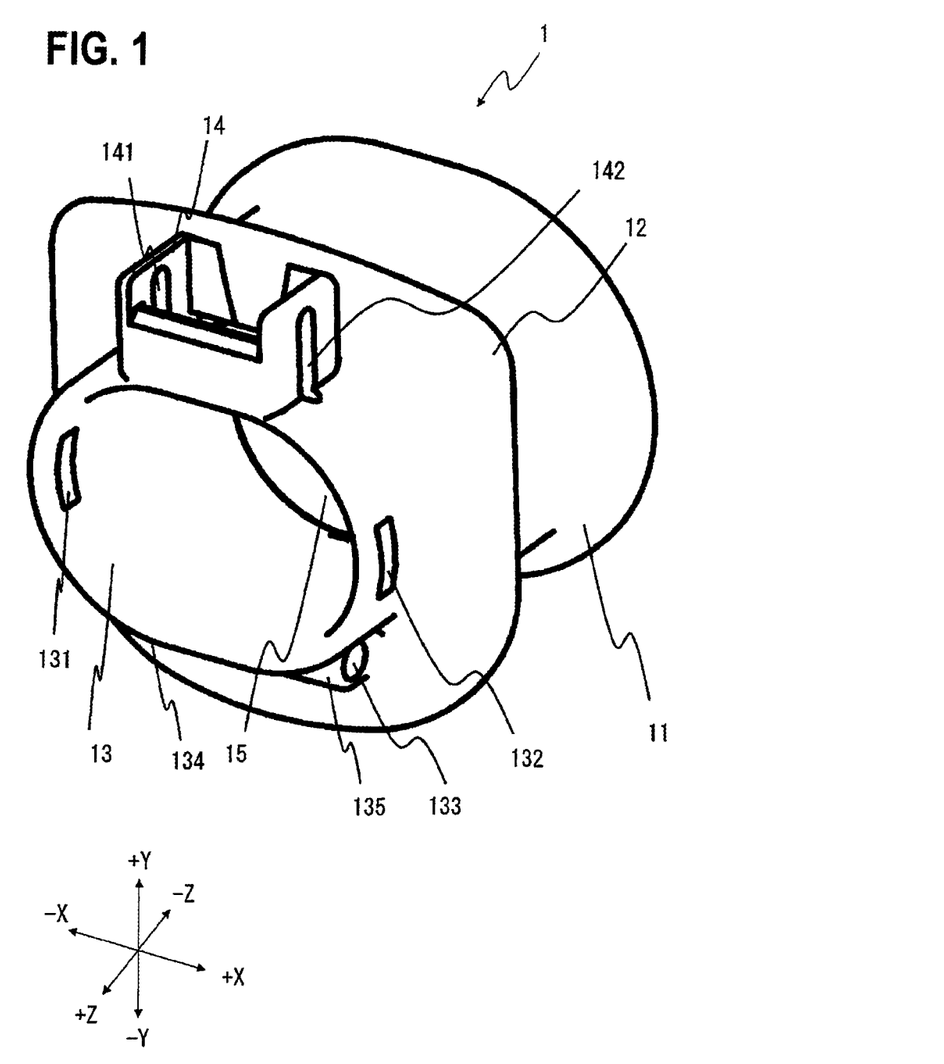
FIG. 1 is a perspective view of a bite block 10 according to a first embodiment.

FIG. 1 is an exploded perspective view schematically illustrating a gas sensor kit 1 according to this embodiment. The gas sensor kit 1 insufflates a therapeutic gas to a subject, and is a medical unit which measures an exhalation gas concentration. The gas sensor kit 1 includes a bite block 10, a nasal adapter 20, a gas sensor 30, and a gas supply unit 40. The therapeutic gas may be an oxygen gas or a hydrogen gas, and in the following description, an oxygen gas is adopted.

The bite block 10 includes an oral cavity insert part 11, a plate 12, an oral cavity outside arrangement part 13, and a connector part 14. In a case where the respiration measurement is not performed when the bite block 10 is used, the bite block 10 may be configured not to have the connector part 14.

The oral cavity insert part 11 is a hollow member which is inserted into the oral cavity of the subject. Preferably, the hollow member has a hollow shape curved to abut on the oral cavity of the subject. In other words, the oral cavity insert part 11 has a hollow shape having a hole 15 which introduces the tube and the like of an endoscope device into a body. The oral cavity insert part 11 may be made, for example, of plastics.

The oral cavity outside arrangement part 13 is a hollow member which communicates with the hole 15 which is the hole through which the tube or the like is introduced in a body, of the oral cavity insert part 11. The oral cavity outside arrangement part 13 has at least one through hole on the side surface which is exposed outside at the time of mounting. In the example of FIG. 1, a through hole 131, a through hole 132, and a through hole 133 are provided. The through hole 131 and the through hole 132 are locking holes which act as a connection mechanism when connected with the external device such as the overtube. The overtube will be described later with reference to FIG. 12. In this example, when a state where the bite block 10 is mounted in the subject is seen from a front view (when the bite block 10 is seen from a positive Z direction), two through holes 131 and 132 are provided in a right and left direction (X axial direction) of the face of the subject. Through the through holes 131 and 132, the hole 15 communicates with the outer surface of the oral cavity outside arrangement part 13.

The through hole 133 which is connected with the tube which supplies a therapeutic gas is provided in a tube introduction part 135. The through hole 133 is a through hole which is connected with the tube for a therapeutic gas, so that the oxygen gas is introduced into the oral cavity. The configuration of the through hole 133 will be described later with reference to FIGS. 9 to 11. Hereinafter, an oxygen tube is adopted as the tube. The therapeutic gas may be a hydrogen gas or the like, but in the following description, an oxygen gas is adopted.

The opening surface 134, which is an end surface in the positive Z direction, of the oral cavity outside arrangement part 13 is not limited, but, preferably, may be a planar shape as illustrated. The planar shape may include a substantially planar shape. In other words, it is preferable that the opening surface 134 have a shape in which the oral cavity outside arrangement part 13 has no concavo-convex portions which catch the tube for an endoscope or the like.

The plate 12 is a member which is formed in a flange shape (in other words, a shape provided to protrude in the X axial direction and a Y axial direction) extending from the oral cavity insert part 11. In a case where the bite block 10 is attached to the subject, the surface of the plate 12 on the oral cavity insert part 11 side abuts on (or approaches) the lip or the teeth of the subject, and the opposing surface does not touch the lip or the teeth of the subject. When the flange-shaped plate 12 is disposed, a portion of the oral cavity outside arrangement part 13 (the positive Z side from the plate 12) becomes exposed to the outside at the time of the attachment.

The connector part 14 is provided at the upper side (positive Y direction) of the oral cavity outside arrangement part 13. The connector part 14 is a connection mechanism with a nasal adapter 20 or another adapter. The nasal adapter 20 is described later with reference to FIG. 2. In this example, the connector part 14 has an attaching hole 141 and an attaching hole 142 which oppose to each other along the X direction. When a boss of the nasal adapter 20 and the like are fitted to the attaching holes 141 and 142, the nasal adapter 20 is connected with the bite block 10.

As illustrated in the drawings, the attaching hole 141 and the attaching hole 142 desirably has an elongated shape in which the Y axial direction is a major axis. By the elongated shape, the nasal adapter 20 is movable in an upper and lower direction (Y axial direction), and can adjust the degree of contact between the nasal adapter 20 and the bite block 10 according to the size and the like of the face of the subject. A major axis direction of the attaching holes 141 and 142 may not be necessarily a direction orthogonal to the Z axis, and is configured such that the height which is the length of the attaching holes 141 and 142 in the Y axial direction is larger than the width which is the length of the attaching holes 141 and 142 in the Z axial direction.

Figure 2:
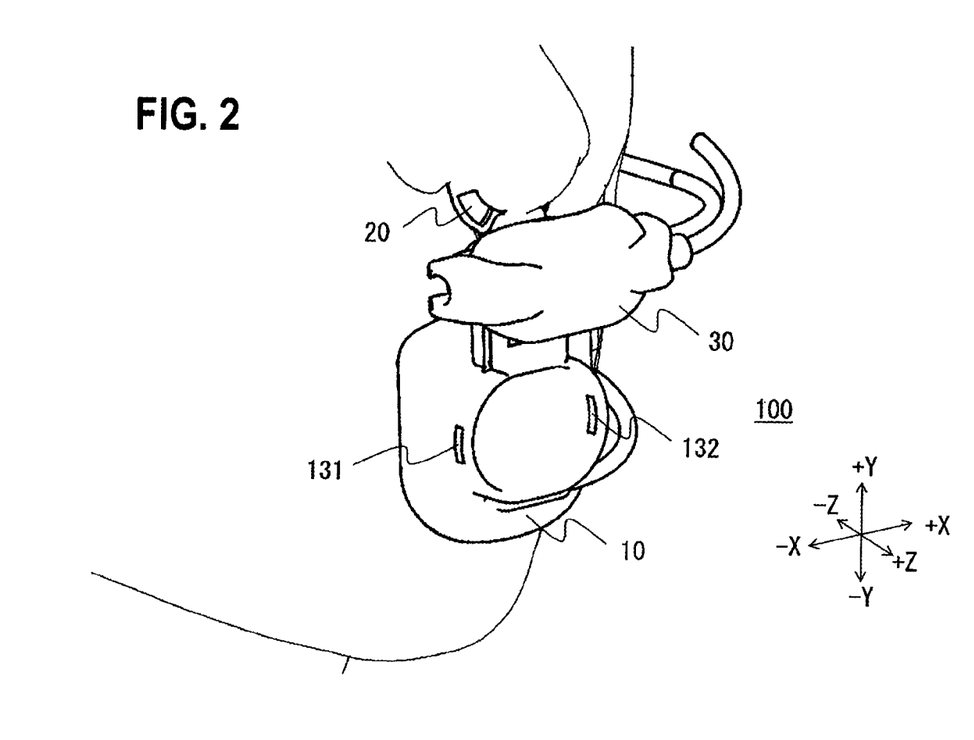
FIG. 2 is a conceptual view illustrating an appearance when the bite block 10 according to the first embodiment is mounted.

The mounted state of the bite block 10 will described with reference to FIG. 2. FIG. 2 illustrates an example in which the nasal adapter 20 and the gas supply unit 30 are attached in the bite block 10. In FIG. 2, a portion of the nasal adapter 20 is overlapped with the gas supply unit 30 and not shown therein. The gas supply unit 30 is a unit which supplies the oxygen through an oxygen tube 31 and may not be provided in a certain treatment purpose. That is, FIG. 2 illustrates an appearance of the gas sensor kit 100 having the bite block 10 and the nasal adapter 20. Two nasal tubes of the nasal adapter 20 are disposed in the vicinity of the nostrils of the subject.

As illustrated in the drawings, the oral cavity outside arrangement part 13 is configured to be exposed outside the oral cavity of the subject. For this reason, the through holes 131 to 133 are exposed outside the oral cavity of the subject.

In other words, the through holes 131 to 133 are provided in the outer exposed surface of the oral cavity outside arrangement part 13.

Figure 3:
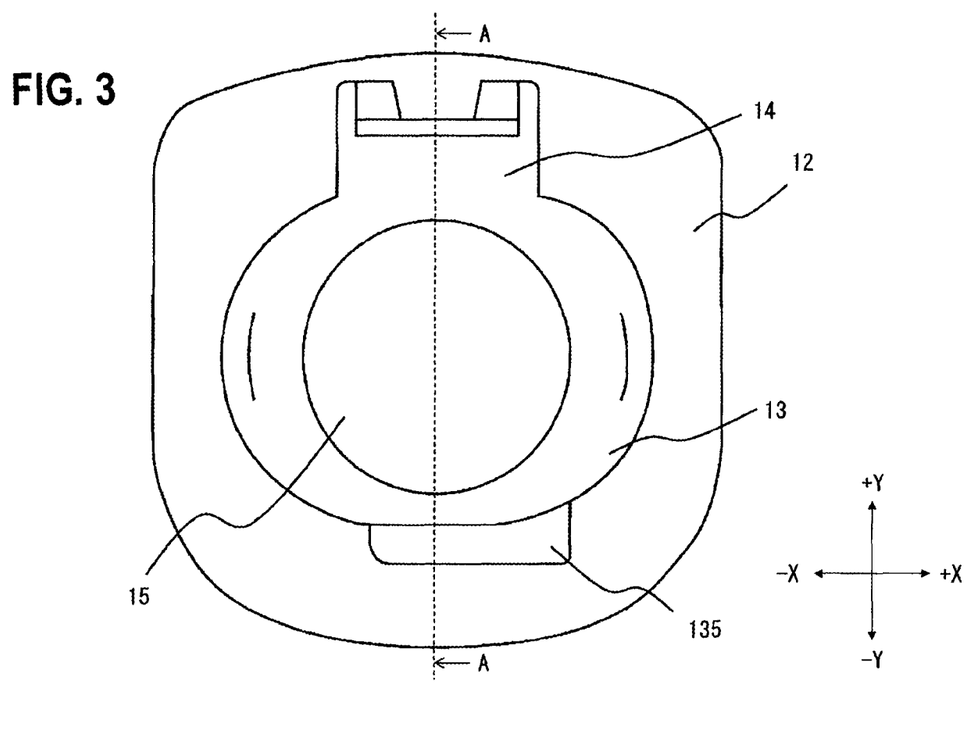
FIG. 3 is a front view of the bite block 10 according to the first embodiment.

Subsequently, the configuration of the bite block 10 will be further described with reference to six drawings of FIGS. 3 to 8. FIG. 3 is a front view of the bite block 10 (a view when the bite block 10 is seen from the positive Z direction). As illustrated in the drawing, the hole 15 is provided in a substantially central position (central positions of an X axis and a Y axis) in vertical and lateral directions when attached to the subject, and the oral cavity outside arrangement part 13 is provided to surround the hole 15. The tube introduction part 135 provided with the through hole 133 (not illustrated in FIG. 3) is disposed in the lower portion (negative Y direction) of the oral cavity outside arrangement part 13, and the connector part 14 is disposed in the upper portion (positive Y direction).

Figure 4:
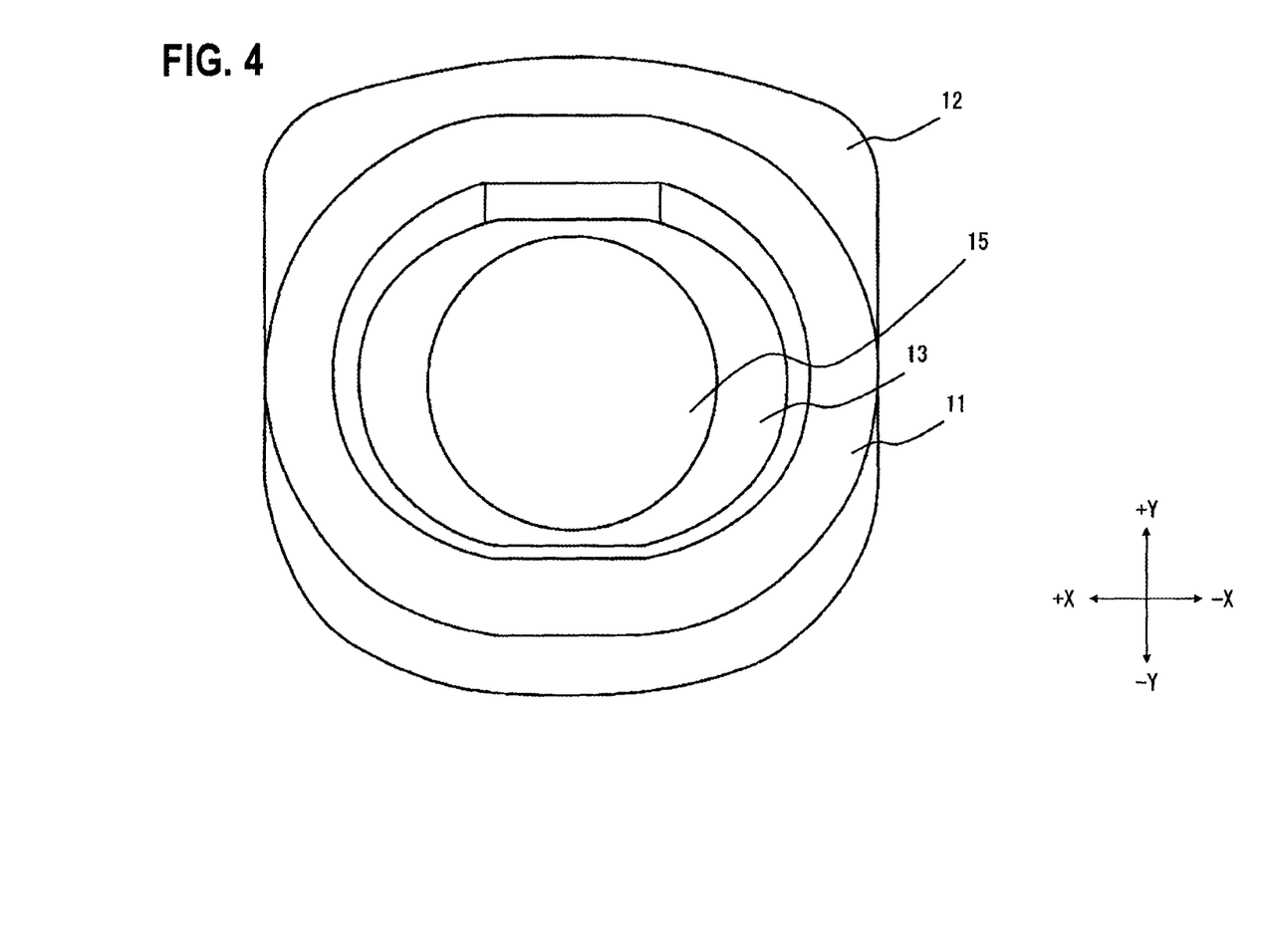
FIG. 4 is a back view of the bite block 10 according to the first embodiment.

FIG. 4 is a back view of the bite block 10 (a view when the bite block 10 is seen from the negative Z direction). Similarly to FIG. 3, the hole 15 is disposed in a substantially central position in the vertical and lateral directions when attached to the subject. The oral cavity outside arrangement part 13 and the oral cavity insert part 11 are disposed to surround the hole 15.

Figure 5:
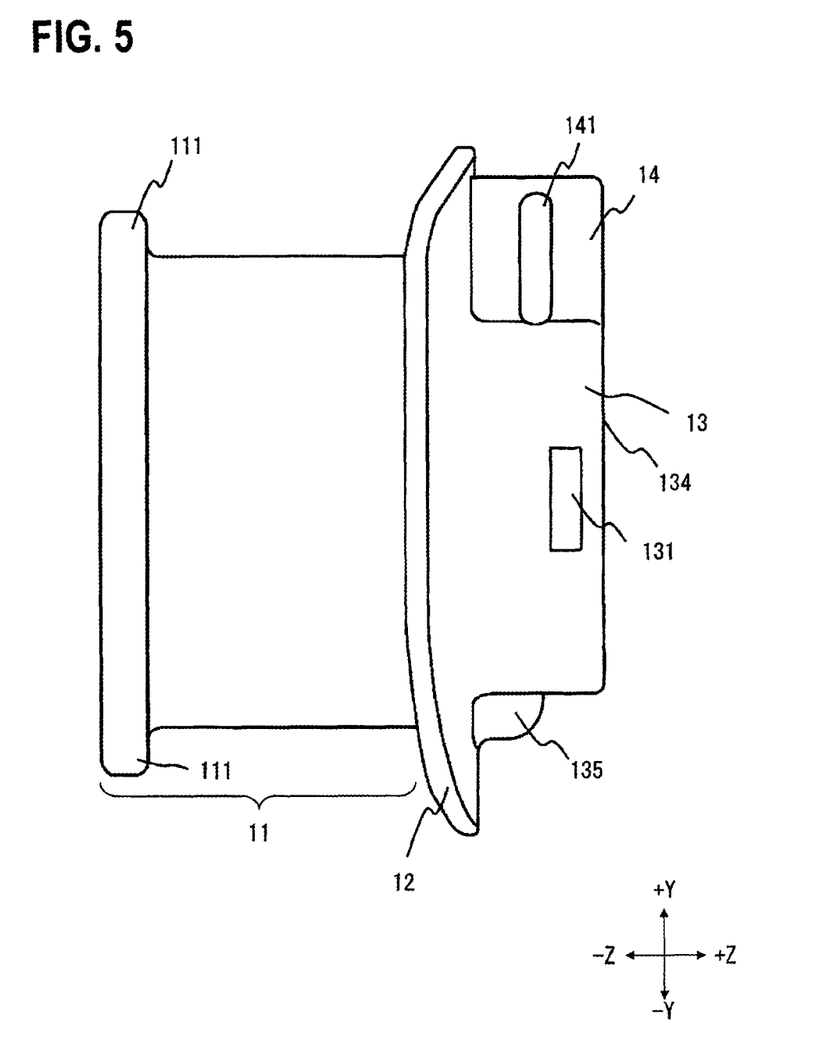
FIG. 5 is a right side view of the bite block 10 according to the first embodiment.

FIG. 5 is a right side view of the bite block 10 (a view when the bite block 10 is seen from the negative X direction). The plate 12 is provided to protrude from the oral cavity insert part 11. In addition, when seen from the right side surface, the upper end and the lower end of the plate 12 have a curved shape. However, the invention is not necessarily limited thereto, and any shape of the plate 12 may be adopted as long as the plate 12 separates the oral cavity insert part 11 and the oral cavity outside arrangement part 13.

The oral cavity insert part 11 is a hollow member in which the Z axial direction is set as a height. The oral cavity insert part 11 has a convex portion 111 which is convex in a direction away from the hole 15 (in the Y axial direction in FIG. 5). When the convex portion 111 is provided, even in a case where the subject coughs or chokes, the convex portion 111 is caught in the oral cavity (lip or teeth) of the subject, so as to prevent the unintentional removal of the bite block 10.

The oral cavity outside arrangement part 13 is a hollow member which extends from the plate 12 in the positive Z direction. The oral cavity outside arrangement part 13 is a structure in which a portion is exposed on the outer side (positive Z side) from the plate 12 (described also in FIG. 9). The through hole 131 is provided in a side surface portion (outer exposed surface) of the oral cavity outside arrangement part 13. The through hole 131 is a hole through which the outer surface of the oral cavity outside arrangement part 13 communicates with the hole 15. The connector part 14 is provided in the upper portion (positive Y direction) of the oral cavity outside arrangement part 13. The elongated attaching hole 141 is provided in the connector part 14.

Figure 6:
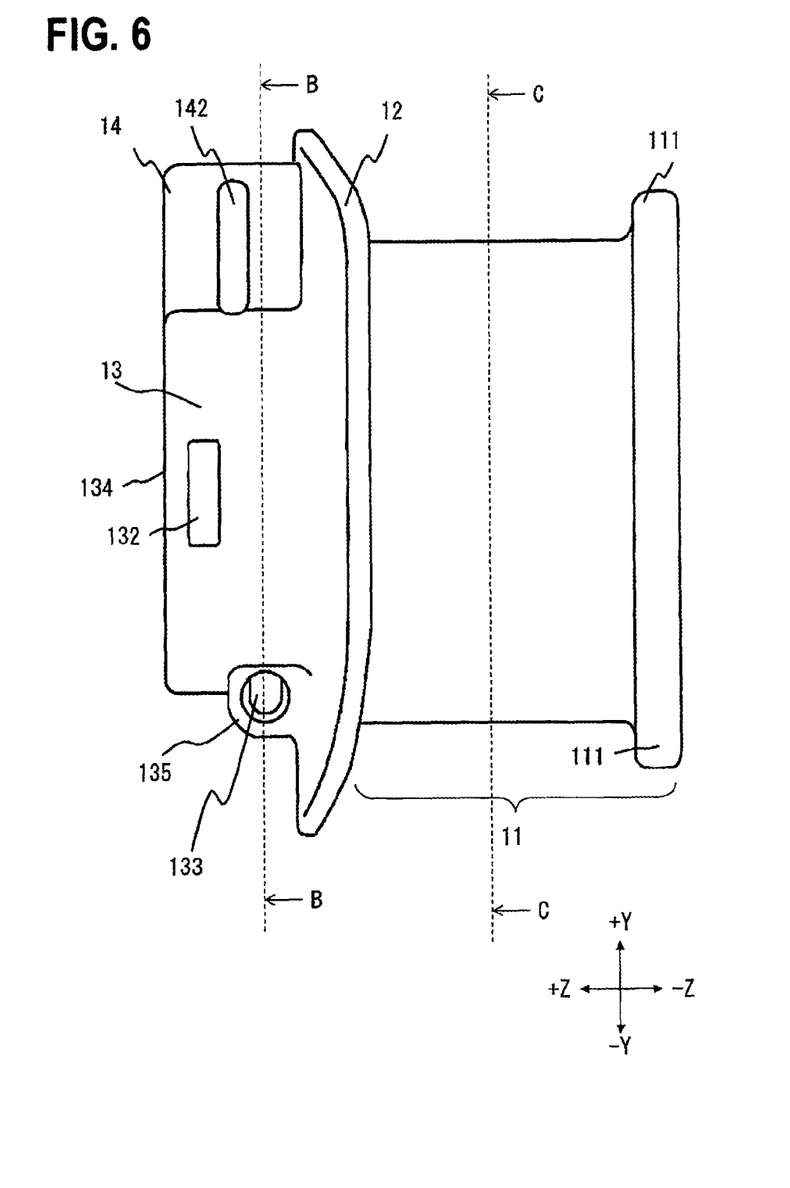
FIG. 6 is a left side view of the bite block 10 according to the first embodiment.

FIG. 6 is a left side view of the bite block 10. In other words, FIG. 6 is a view when the bite block 10 is seen from the positive X direction. Herein, the description will be given about points different from FIG. 5. The through hole 132 is provided in the side surface portion of the oral cavity outside arrangement part 13. The through hole 132 is a hole through which the outer surface of the oral cavity outside arrangement part 13 communicates with the hole 15. The tube introduction part 135 has the through hole 133 which is attachable and detachable to/from the oxygen tube. The through hole 133 is a hole as a flow path through which the therapeutic gas is introduced in the oral cavity of the subject. The detail configuration of the through hole 133 will be described with reference to the sectional views of FIGS. 9 to 11.

Figure 7:
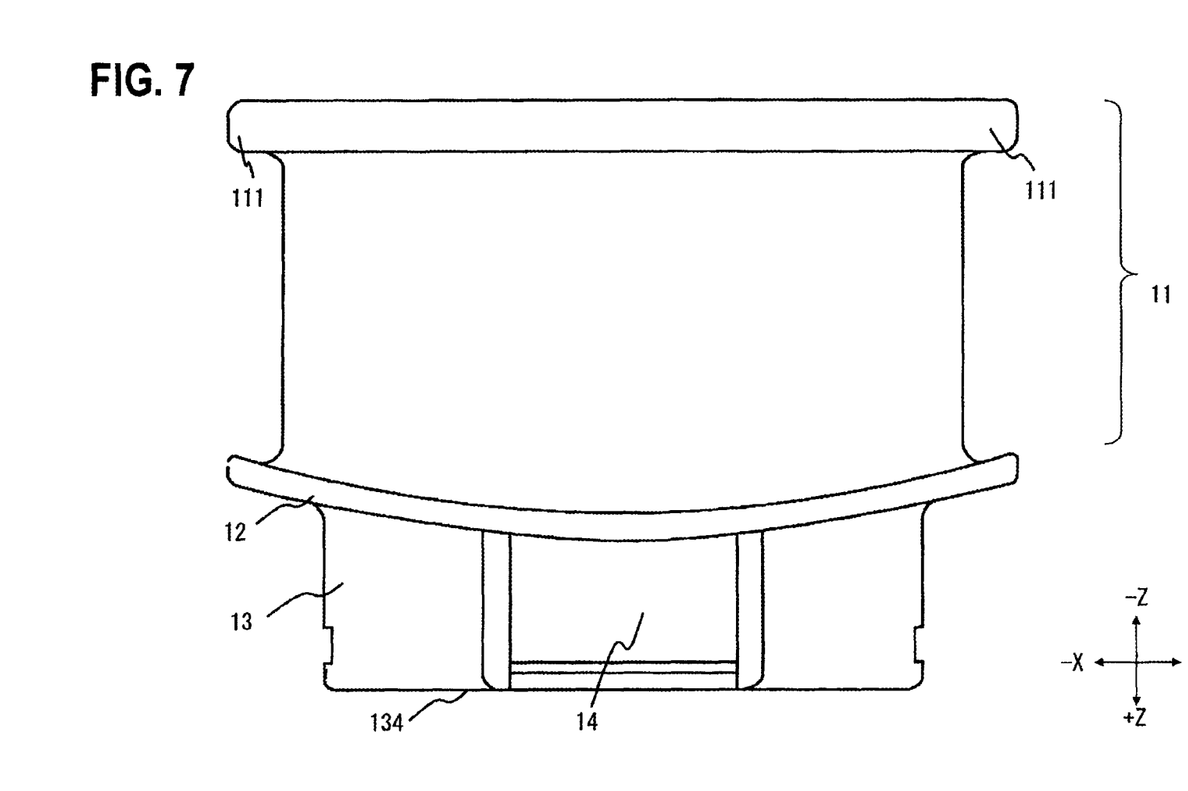
FIG. 7 is a top view of the bite block 10 according to the first embodiment.

FIG. 7 is a top view of the bite block 10 (a view when the bite block 10 is seen from the positive Y direction). When seen from the upper surface, the connector part 14 which is connected with the nasal adapter 20 and the like is provided in the oral cavity outside arrangement part 13. The plate 12 has a shape in which the center is curved (bent) in the positive Z direction. The shape of the plate 12 is not limited to that of FIG. 7, but such a curved shape makes the plate 12 be easily fitted to the lip of the subject.

Figure 8:
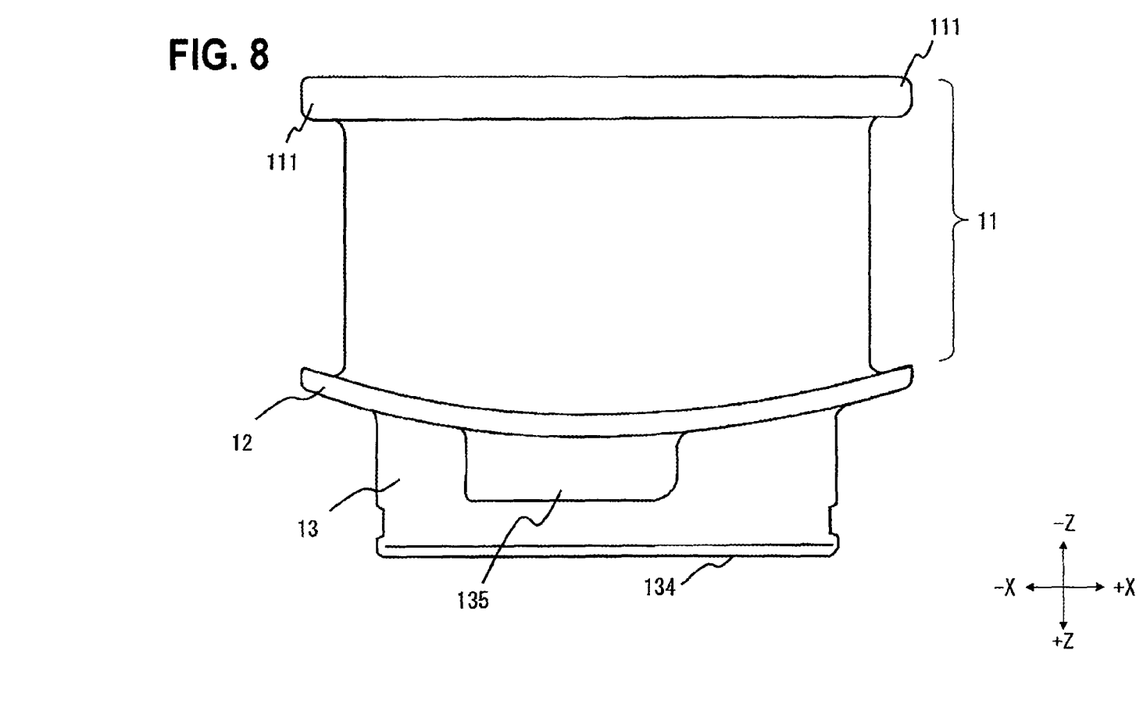
FIG. 8 is a bottom view of the bite block 10 according to the first embodiment.

FIG. 8 is a bottom view of the bite block 10 (a view when the bite block 10 is seen from the negative Y direction). When seen from the lower surface, the tube introduction part 135 is provided in the oral cavity outside arrangement part 13.

Figure 9:
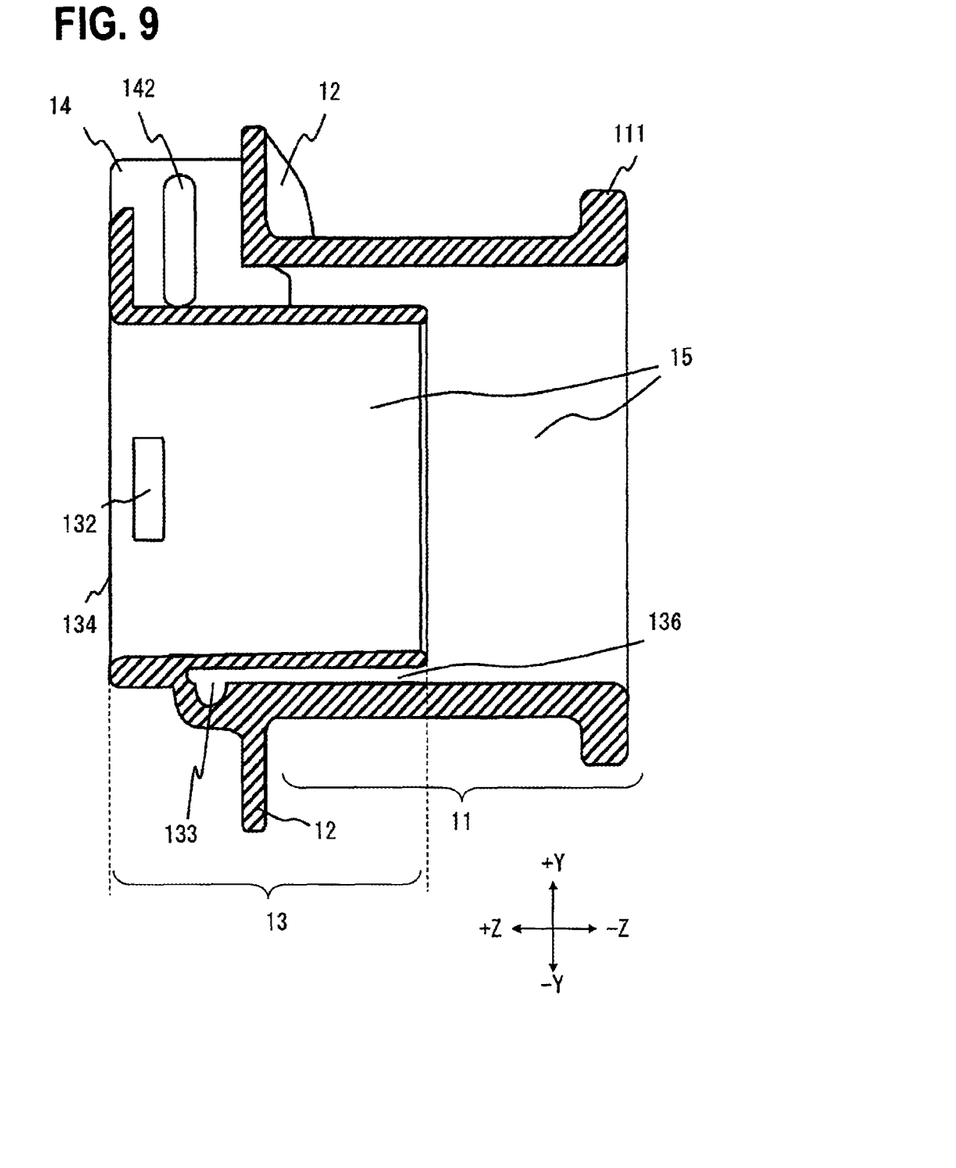
FIG. 9 is a sectional view of the bite block 10 according to the first embodiment.
Figure 10:
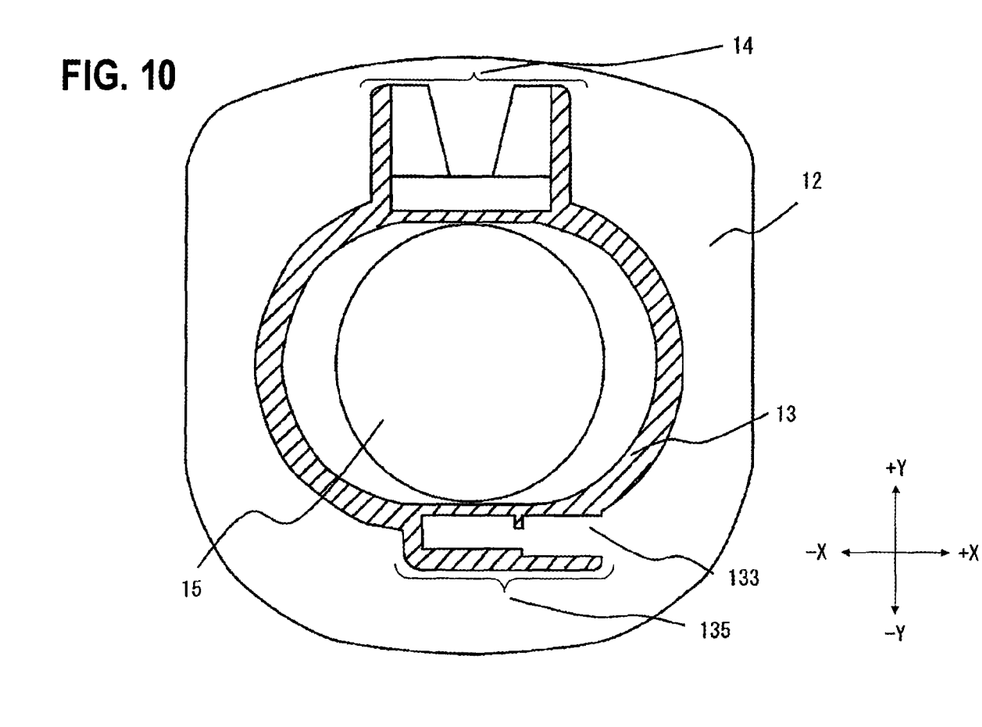
FIG. 10 is a sectional view of the bite block 10 according to the first embodiment.
Figure 11:
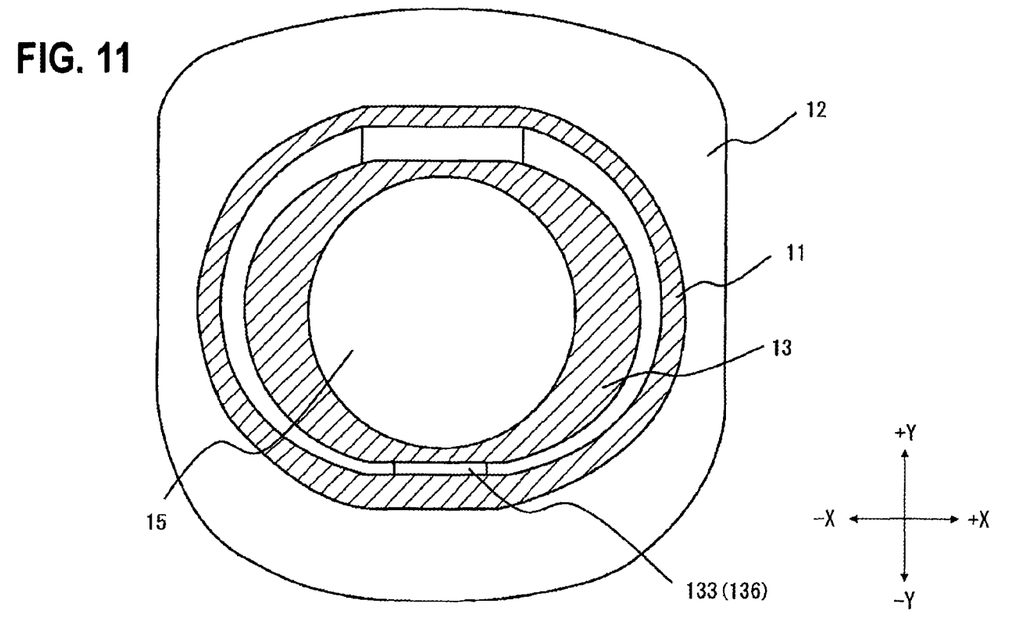
FIG. 11 is a sectional view of the bite block 10 according to the first embodiment.

Subsequently, the structure of the hole 15 or the through hole 133 will be described with reference to the sectional views of FIGS. 9 to 11. FIG. 9 illustrates a sectional surface taken along line A-A in FIG. 3. FIG. 10 illustrates a sectional surface taken along line B-B in FIG. 6. FIG. 11 illustrates a sectional surface taken along line C-C in FIG. 6.

The through hole 133 extends from the positive X direction to the negative X direction (FIG. 10), and a flow path 136 is connected to the extended end (the end in the negative X direction) (FIGS. 9 and 10). The flow path 136 extends in the negative Z direction to communicate with the hole 15 (FIG. 9). That is, the through hole 133 is one aspect of a gas introduction hole through which the hole 15 communicates with the oral cavity outside arrangement part 13. As illustrated in FIG. 11, the through hole 133 (in other words, flow path 136) becomes a gap provided between the oral cavity insert part 11 and the oral cavity outside arrangement part 13.

With reference to FIG. 9, the hole 15 is disposed such that the oral cavity outside arrangement part 13 communicates with the oral cavity insert part 11. The opening surface 134 (terminal end surface on the positive Z side of the hole 15) has a planar shape. When the bite block 10 is mounted, the plate 12 is caught in the vicinity of the lip of the subject although the subject bites the bite block 10 deeply. The oral cavity outside arrangement part 13 has a structure in which a portion is exposed on the outer side (positive Z side) from the plate 12. For this reason, at least a portion of the oral cavity outside arrangement part 13 becomes exposed outside the oral cavity. The through hole 131 (not illustrated in FIG. 9), the through hole 132, and the through hole 133 are provided in the exposed area.

Figure 12:
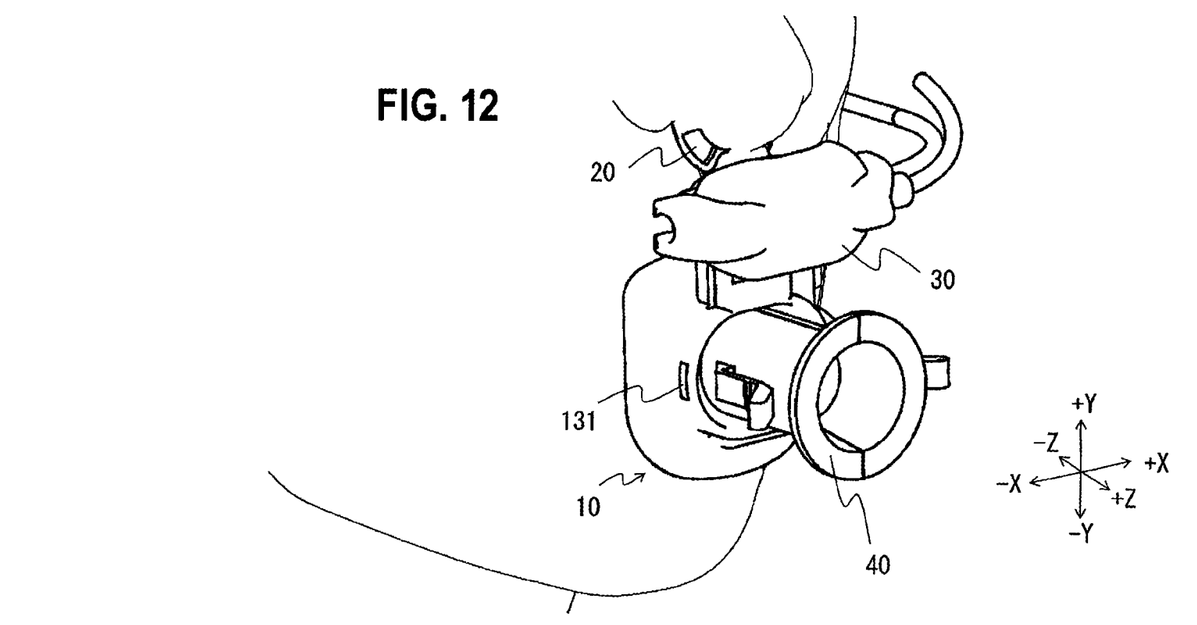
FIG. 12 is a conceptual view illustrating an appearance when the bite block 10 according to the first embodiment is mounted.

Subsequently, the description will be given with reference to FIG. 12 about the mounted state when the overtube 40 is connected to the bite block 10. The overtube 40 is one aspect of an external device. In the overtube 40, a convex portion or a boss for attaching is inserted into the through hole 131 and the through hole 132 (not illustrated in FIG. 12). Accordingly, the overtube 40 is connected with the bite block 10. The overtube 40 may be adopted as long as the overtube is connected with the bite block 10 through the through holes 131 and 132, and may be fixed with respect to the through holes 131 and 132 by any method (including, for example, inserting and fitting, external fitting, fitting, tight fitting, engaging, and occluding).

Subsequently, the description will be given about the effect of the bite block 10 according to this embodiment. The bite block 10 has a configuration in which the through holes 131 to 133 are provided in the oral cavity outside arrangement part 13 exposed outside at the time of mounting. The through holes 131 to 133 act as a connection mechanism which connects the bite block 10 and the external device (such as the overtube and the oxygen tube). When the connection mechanism acts with the through holes 131 to 133, it is possible to simplify the shape of the opening surface 134 of the oral cavity outside arrangement part 13. Accordingly, it is possible to avoid that the soft tube is caught thereby at the time of the endoscope diagnosis.

Since the oral cavity outside arrangement part 13 which is partitioned from the oral cavity insert part 11 by the flange-shaped plate 12 and is exposed to the outside has the through holes 131 to 133, it can be easily perceived whether the bite block 10 is connected with the external device, and the attachment and detachment of the external device can be easily performed. For example, even in a case where there is a need that the overtube or the oxygen tube is connected after the bite block 10 is mounted, the external device can be attached to the outside-exposed through holes 131 to 133. In other words, the external device can be attached in a state where the subject wears the bite block 10.

Since the flange-shaped plate 12 acts as a wall, it is possible to reduce the effect (for example, the saliva is mixed into the oxygen tube) of the saliva.

Particularly, the opening surface 134 of the oral cavity outside arrangement part 13 preferably has a planar shape (FIG. 5 and the like). When the opening surface 134 has the planar shape, a risk that the soft tube is caught in the opening surface 134 is reduced even in a case where a treatment of the endoscope or the like is performed. That is, it is possible to smoothly realize the treatment of the endoscope or the like.

When a state where the bite block 10 is attached to the subject is seen from a front view, the through hole 131 and the through hole 132 are provided in the left and right direction of the face of the subject, respectively. Accordingly, it is possible to firmly lock the overtube (or a similar external device) from both sides.

The through hole 133 acts as a gas introduction hole which introduces the therapeutic gas to the oral cavity. When the therapeutic gas is taken into the through hole 133, the subject can inhale the therapeutic gas (for example, oxygen) also from the oral cavity.

The bite block 10 has the connector part 14 with which the nasal adapter 20 is connected, and the connector part 14 has the attaching holes 141 and 142 in which the nasal adapter 20 is attached. Accordingly, it is possible to attach and detach the bite block 10 and the nasal adapter 20 according to the use.

Hereinbefore, the invention made by this inventor is described in specific on the basis of the embodiment. However, the present invention is not limited to the above-described embodiment, and the invention may be modified variously without departing from the spirit and scope of the invention.

For example, assuming the use in a case where the oxygen is not supplied, the bite block 10 may be configured not to have the through hole 133. In addition, the bite block 10 may be configured to have only the through hole 131 for connection with the overtube. In other words, the bite block 10 may be connected with the overtube merely by fitting one through hole 131.

The bite block 10 may be connected with the overtube by providing a groove instead of the through hole 131 or 132. That is, the bite block 10 is configured such that at least one hole or groove which is connected with the external device (overtube and the like) is provided in the outer surface of the oral cavity outside arrangement part 13.

Similarly, assuming the use in a case where the overtube is not connected, the bite block 10 may be configured not to have the through holes 131 and 132 (to have only the through hole 133 which is connected with the tube).

The present application is based on Japanese Patent Application No. 2016-117770, filed on Jun. 14, 2016, the entire contents of which are incorporated herein by reference.

INDUSTRIAL APPLICABILITY

There is provided with a bite block having a structure which is proper for connection with the external device such as the overtube or the oxygen tube, and the gas sensor kit.

REFERENCE SIGNS LIST

10: bite block
11: oral cavity insert part
12: plate
13: oral cavity outside arrangement part
131 to 133: through hole
134: opening surface
135: tube introduction part
14: connector part
141, 142: attaching hole
15: hole
151, 152: boundary line
20: nasal adapter
30: oxygen supply unit
40: overtube
100: gas sensor kit

The invention claimed is:

1. A bite block comprising:
a tubular oral cavity insert part that is in contact with an oral cavity of a subject at the time of attaching the bite block to the subject;
a plate that is formed in a flange shape extending from the oral cavity insert part;
a tubular outside part that includes an exposed portion which is exposed to an outside of the oral cavity at the time of attaching, and communicates with a hole of the oral cavity insert part; and
a connector part including an attachment mechanism to which a nasal adapter is attachable, the connector part being opposed to a side surface of the tubular outside part,
wherein the tubular outside part includes at least one through hole or groove on the exposed portion with which an external device is attachable to the bite block
wherein the plate is configured to separate the oral cavity insert part and the at least one through hole or groove on the tubular outside part,
wherein the at least one through hole or groove is formed on a side surface of the tubular outside part,
wherein the attachment mechanism is elongated in a predetermined direction, and
wherein the nasal adapter is attached to the attachment mechanism such that the nasal adapter is movable in the predetermined direction in a state where a part of the nasal adapter is fitted into the attachment mechanism.

2. The bite block according to claim 1, wherein
an opening surface of the tubular outside part has a planar shape.

3. The bite block according to claim 1, wherein the attachment mechanism includes an attachment hole configured for attaching the nasal adapter to the bite block, the attachment hole being elongated in the predetermined direction.

4. The bite block according to claim 3, wherein
the attachment hole has an elongated shape having a minor axis and a major axis.

5. The bite block according to claim 1, wherein
the tubular oral cavity insert part has a cylindrical shape.

6. The bite block according to claim 1, wherein
the tubular outside part has a cylindrical shape.

7. A gas sensor kit, comprising:
the bite block according to claim 1; and
the nasal adapter, wherein the nasal adapter is attached to the attachment mechanism of the connector part such that the nasal adapter is disposed in a vicinity of a nostril in the state where the bite block is attached to the subject.

8. A gas sensor kit comprising:
the bite block according to claim 1; and
the external device, wherein the external device is attached to the at least one through hole or groove of the tubular outside part.

9. The bite block according to claim 1, wherein the bite block includes at least two through holes or grooves provided in a right and left direction of a face of the subject in a state where the bite block is attached to the subject and is viewed from a front side of the subject.

10. The bite block according to claim 1, wherein the tubular outside part includes a gas introduction hole that introduces a gas to the oral cavity of the subject.

11. The bite block according to claim 1, wherein the connector part and the tubular oral cavity insert part are arranged on opposites sides of the plate.

* * * * *